United States Patent [19]

Narula et al.

[11] Patent Number: 5,536,857
[45] Date of Patent: Jul. 16, 1996

[54] SINGLE SOURCE VOLATILE PRECURSOR FOR $SiO_2.TiO_2$ POWDERS AND FILMS

[75] Inventors: Chaitanya K. Narula, Ann Arbor, Mich.; Ashima Varshney, Hackensack, N.J.; Umar Riaz, Ann Arbor, Mich.

[73] Assignee: Ford Motor Company, Dearborn, Mich.

[21] Appl. No.: 270,943

[22] Filed: Jul. 5, 1994

[51] Int. Cl.[6] .................... C07F 7/00; C07F 7/02; C07F 7/28
[52] U.S. Cl. ............................................................ 556/10
[58] Field of Search ....................................... 556/10

[56] References Cited

U.S. PATENT DOCUMENTS

| Re. 29,948 | 3/1979 | Dwyer et al. | 208/110 |
|---|---|---|---|
| 3,582,395 | 6/1971 | Adams et al. | 117/124 |
| 3,941,871 | 3/1976 | Dwyer et al. | 423/326 |
| 3,993,835 | 11/1976 | Miedaner | 428/378 |
| 4,232,062 | 11/1980 | Okino et al. | 427/160 |
| 4,333,881 | 6/1982 | Greco et al. | 260/429 R |
| 4,347,347 | 8/1982 | Yajima et al. | 528/30 |
| 4,361,691 | 11/1982 | Yajima et al. | 528/28 |
| 4,400,327 | 8/1983 | Baskent et al. | 260/429 R |
| 4,410,501 | 10/1983 | Taramasso et al. | 423/326 |
| 4,424,320 | 1/1984 | McDaniel | 526/106 |
| 4,458,027 | 7/1984 | Berge et al. | 502/104 |
| 4,547,557 | 10/1985 | McDaniel | 526/106 |
| 4,701,428 | 10/1987 | Bellussi et al. | 502/8 |
| 4,711,869 | 12/1987 | Cullo et al. | 502/239 |
| 4,720,472 | 1/1988 | Parrott | 502/211 |
| 4,954,653 | 9/1990 | Bellussi et al. | 564/223 |
| 4,981,831 | 1/1991 | Knudsen et al. | 502/236 |
| 5,162,283 | 11/1992 | Moini | 502/236 |
| 5,169,969 | 12/1992 | Sherif | 556/28 |
| 5,194,990 | 3/1993 | Boulos et al. | 359/587 |

FOREIGN PATENT DOCUMENTS 0294830 6/1988 European Pat. Off. .

OTHER PUBLICATIONS

European Search Report, Application No. EP95304695.0, dated Oct. 7, 1995, 3 pages.

Chemical Abstracts, vol. 115, No. 8, 1991, Aug. 26, Columbus, Ohio, USA, E. A. Mazurenko et al: "Products of Hydrolytic Condensation of Silicone and Titanium Ethoxides" Page 886, No. 84 21Ox & Ukr. Khim. Zh. 1991, 57(1), 3–5 (Russ. Ed.).

Primary Examiner—Porfirio Nazario-Gonzales
Attorney, Agent, or Firm—Lorraine S. Melotik; Roger L. May

[57] ABSTRACT

Novel single-source volatile precursor compounds are disclosed, having the general formula

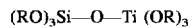

$$(RO)_3Si-O-Ti(OR)_3$$

where each of the six R moieties in the $C_3$ to $C_6$ alkyl, preferably all being tert-butyl. The precursor compounds are suitable for use in dissociation methods, such as sol-gel and chemical vapor deposition, for preparing powders and films of stoichiometric $SiO_2.TiO_2$. Optical films to provide an anti-reflective surface on a lens, window or the like and powders for catalytic substrates, etc. are prepared using the $SiO_2.TiO_2$ yielded by the single-source volatile precursor compound.

1 Claim, No Drawings

SINGLE SOURCE VOLATILE PRECURSOR FOR SIO₂.TIO₂ POWDERS AND FILMS

INTRODUCTION

The present invention is directed to single source precursor compounds for producing $SiO_2.TiO_2$ films, powders and the like by chemical vapor deposition ("CVD"), sol-gel processes and the like.

BACKGROUND OF THE INVENTION

Silica-titania, $SiO_2 \cdot xTiO_2$, powders and films have well known commercial applications. Powders have applications as washcoats for the preparation of catalyst substrate materials useful in motor vehicle catalytic converters and the like, since they have been shown to assist in catalytic hydrogenation of CO. In addition, $SiO_2.TiO_2$ optical films are known to have a high refractive index to provide useful anti-reflective properties suitable for motor vehicle and architectural glazing applications.

Recently, heterometallic alkoxides have been shown to be useful precursors for the preparation of multi-component metal-oxide powders and films via sol-gel processes. A large number of heterometallic alkoxides of the formula $[L_mM—(OR)_2—M'L'_n]$ are known Mehrotra et al, *Mat. Res. Soc. Symp. Proc.*, 121 (1988) 81; D. C. Bradley et al., Metal Alkoxides, Academic Press, NY, (1978). K. G. Caulton et al., Chem. Rev. 90 (1990) 969. Applicable to the production of $SiO_2.TiO_2$ films and powders, however, such heterometallic alkoxides of silicon are largely unknown. Moreover, use of such heterometallic alkoxides in CVD for production of multi-component metal-oxide films has generally resulted in the stoichiometry of the metals in the precursor compounds, that is, in the parent alkoxides, not being retained in the resultant films. D. C. Bradley, Chem. Rev. 89 (1989) 1317. As a possible explanation of this loss of stoichiometry, it has been suggested that the heterometallic alkoxide precursors dissociate into component alkoxides of different volatility resulting in the loss of stoichiometry in films.

Known methods of producing $SiO_2.xTiO_2$ powders and films employ multiple precursor compounds: a first precursor compound as a source of silicon and a second precursor compound as a source of titanium. Maintaining uniformity and/or stoichiometry of $SiO_2.TiO_2$ throughout the resultant powders and films has proved difficult. The need for exacting control of multiple process parameters to achieve desired stoichiometry and/or uniformity causes increased cost and complexity. Precursors containing silicon and titanium are needed which furnish products in desired forms containing the precursor stoichiometry of silicon and titanium. It is an object of the present invention to provide $SiO_2.TiO_2$ materials and single source precursor compounds for preparing films and powders of $SiO_2.TiO_2$ retaining the stoichiometry of the precursors. These and other objects and advantages of the invention will be apparent from the following disclosure.

SUMMARY OF THE INVENTION

In accordance with a first aspect of the invention, novel single source volatile precursor compounds are provided for preparing stoichiometric $SiO_2.TiO_2$ materials. That is, both silicon and titanium are provided by the same precursor compound for preparing $SiO_2.TiO_2$ materials, such as powders by a sol-gel process, film by a CVD process and the like. The novel precursor compounds have the general formula

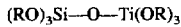

$(RO)_3Si—O—Ti(OR)_3$ where each of the six R groups is $C_3$ to $C_6$ alkyl, preferably $C_4$ to $C_6$ alkyl. In preferred embodiments all six of the R groups of the compound are the same, most preferably being tert-butyl. That is, most preferably the novel single source volatile precursor compound has the formula $(^tBuO)_3Si—O—Ti(OBu^t)_3$.

The alkoxy groups are selected for ease of synthesis of the precursor compound, stability of the precursor compound at ambient temperatures during storage and use in producing $SiO_2.TiO_2$, and for application suitability. Application suitability here refers to the processing technique intended for the preparation of $SiO_2.TiO_2$ materials, for example, pyrolysis or the like for preparation as a powder and chemical vapor deposition or the like for preparation as a film. Thus, it refers, for example, to suitable volatility for use in a chemical vapor deposition process for the production of $SiO_2.TiO_2$ films or suitable solubility in inert solvents for use in a sol-gel process for the production of $SiO_2.TiO_2$ powders. The R groups are selected generally to provide good stability of the precursor, generally requiring that they are sufficiently bulky that the compound does not disproportionate. The aforesaid most preferred single source volatile precursor, $(^tBuO)_3Si—O—Ti(OBu^t)_3$ has excellent stability and provides $SiO_2.TiO_2$ films and powders by the aforesaid preparation methods.

It is a significant advance in the art to provide such heterometallic alkoxide of silicon. This novel precursor compounds can be considered to be a partially hydrolyzed heterometallic alkoxide which, as discussed further below, is useful for the preparation of $SiO_2.TiO_2$ materials. It is noteworthy that compounds of the type $(RO)_3Si—O—M(OR)_n$ are not suitable in most cases for preparation of $SiO_2.MO_n$ materials, because Si—O—M bonds hydrolyze faster than RO—Si bonds do. Without wishing to be bound by theory, it is presently believed that the titanium in the novel precursor compounds of the invention catalyzes and accelerates the hydrolysis of Si—OR bonds, yielding $SiO_2.TiO_2$ materials with uniform distribution of components. Infra-red spectral studies suggest the presence of Si—O—Ti bonds in the resulting powders.

It is significant that compounds of the general formula $(RO)_3Si—O—M(OR)_3$ where M is a metal and the R groups are alkyl or other hydrocarbon moiety, have been found unsuitable in most cases for production of mixed oxide films and powders due, perhaps, to the faster rate at which the RO—M bonds hydrolyze than do the RO—Si bonds. Again, without wishing to be bound by theory, it is presently believed that in the single source precursor compounds of the present invention titanium catalyzes and accelerates the hydrolysis of the RO—Si bonds, yielding $SiO_2.TiO_2$ with uniform distribution of components. In any event, significant advantage is provided, including reduced process complexity, through the use of such silicon/titanium heterometallic alkoxide in the production of $SiO_2.TiO_2$ materials. In particular, particular advantage is achieved in that silicon and titanium are provided by the volatile precursor compound in a uniform 1:1 ratio.

In accordance with a second aspect, a method is provided for the preparation of $SiO_2.TiO_2$ powders and films comprising exposing the precursor compound $(RO)_3Si—O—Ti(OR)_3$ to appropriate conditions. In accordance with one embodiment, stoichiometric $SiO_2.TiO_2$ is prepared as a powder by a sol-gel process comprising forming a solution of the precursor compound in suitable solvent, such as tetrahydrofuran, adding water mixed with additional solvent to the precursor solution at reduced temperature to form a gelable solution, warming the gelable solution to form a gel, and removing volatiles from the gel to form a powder consisting essentially of stoichiometric $SiO_2.TiO_2$. The powder so produced can be used in producing catalyst substrate materials, most particularly in an automotive exhaust reduction catalyst washcoat. Films and fibers can also be prepared by the standard technology of sol-gel process from these precursors.

In another preferred embodiment the $SiO_2.TiO_2$ is prepared as a film on a substrate by a chemical vapor deposition process. The substrate is exposed at elevated temperature to a deposition atmosphere comprising vapor generated by heating the precursor compound, preferably to about 60° to 100° C., in a carrier gas, such as nitrogen. The substrate may be selected, for example, from silicon, quartz, glass and the like. Most preferred is production of the film as an optical anti-reflective film having a refractive index between 1.7 and 1.9 on a substrate of substantially transparent soda-lime-silica glass. Reference herein to an "optical" film is intended to mean a film with sufficient clarity and transparency to be suitable for use on a lens or window glass or the like.

In addition to the advantages mentioned above, it is particularly significant that a single precursor is provided as a source for both the silicon and titanium in preparing $SiO_2.TiO_2$, most preferably, 1:1 stoichiometric $SiO_2.TiO_2$. Process complexity and the inherent reduction in process reliability are thereby avoided in controlling the uniformity and quality of presentation of multiple precursor compounds (one to provide silicon and another for titanium). The stoichiometry of silicon and titanium in the precursor (1:1) is retained in the powders prepared by sol-gel process and films prepared by atmospheric pressure CVD ("APCVD") methods under suitable conditions. In addition, it is possible to prepare non-stoichiometric films and powders, preferably by mixing the precursor with $Si(OR)_4$ or $Ti(OR)_4$ prior to preparation of the powders and films, wherein R preferably is as defined above. Varying the temperature and/or other process parameters also furnishes controlled non-stoichiometric films by APCVD methods, etc. These and other features and advantages of the various aspects of the invention will be apparent from the following detailed description of certain preferred embodiments.

DETAILED DESCRIPTION OF CERTAIN PREFERRED EMBODIMENTS

The synthesis of $(RO)_3Si-O-Ti(OR)_3$ preferably proceeds by reaction of $Ti(O^tC_4H_9)_4$ with $(^tC_4H_9O)_3SiOH$ in equimolar ratio. The reaction product is a sharp melting point solid which sublimes under reduced pressure. Elemental analysis of the reaction product has showed it to be pure [tri-(tert-butoxy)siloxy]tri-(tert-butoxy)titanium. Without wishing to be bound by theory, it is presently understood that the reaction proceeds in accordance with the following:

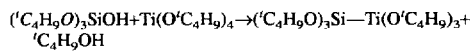

Infrared spectrum analysis of the reaction product exhibits a sharp band at 945 cm$^{-1}$ assignable to Si—O—Ti stretching vibration. *Zeiteler, V. A.; Brown, C. A.; J. Amer. Chem. Soc.*, 61 (1957) 1174. The NMR spectrum of the reaction product solid shows singlets (1.30, 1.29 ppm) for protons of tert-butoxy groups attached to silicon and titanium. The $^{13}C$ NMR spectrum shows singlets (32.11, 31.56 ppm) for methyls of tert-butoxy groups and singlets (81.56, 71.68 ppm) for tertiary carbons. These special data support the formulation to be $(^tC_4H_9O)_3Si-O-Ti(O^tC_4H_9)_3$.

The $(RO)_3Si-O-Ti(OR)_3$ product of the above described synthesis procedure is found to yield gels on careful hydrolysis in tetrahydrofuran (THF). After drying, the gels show negligible organic residues. Without wishing to be bound by theory, it is presently believed that the absence of organic residues indicates titanium catalyzed hydrolysis of alkoxy groups on the silicon moiety, since $Si-O^tC_4H_9$ in $(^tC_4H_9O)_3Si-OH$ is stable even in acidic water. The IR spectrum of the dried gel shows a weak band at 941 cm$^{-1}$ assignable to Ti—O—Si bonds. Thermogravimetric analysis shows a weight loss of 18% in the 50°–330° C. range and 7% in the 400°–700° C. range. An amorphous white powder forms on firing the gel at 500° C. for 2 hours in air. Diffraction peaks due to anatase $TiO_2$ are observed in the X-ray powder diffraction after firing at 700° C. The particle size is calculated to be 84 Å from the Scherrer formula. The transformation to rutile phase is found to commence at 1000° C. The $SiO_2$ component of the gel is found to remain amorphous. Residual Ti—O—Si stretching bands (935–937 cm$^{-1}$) were seen even after high temperature treatment. Elemental analysis of the sample shows a Si:Ti ratio of 1.0:1.08 [Found Si 17.9; Ti 33.3%].

EXAMPLE 1

Preparation of $(^tBuO)_3Si-O-Ti(OBu^t)_3$: To a solution of $Ti(OBu^t)_4$ (5.0 g, 14.7 mmol) in 30 ml of hexane was added a solution of $(^tBuO)_3SiOH$ (3.88 g, 14.7 mmol) in 25 ml of hexane at −40° C. After warming to room temperature and stirring for 3 hrs., volatiles were removed and the residue was sublimed at 100° C./30 mtorr. A yield of 7.0 grams, 89.7%, was obtained and characterized as above to confirm its chemical identity as $(^tBuO)_3Si-O-Ti(OBu^t)_3$.

EXAMPLE 2

Sol-Gel Processed Powder: To a solution of $(^tBuO)_3Si-O-Ti(OBu^t)_3$ (1.53 g) prepared as in Example 1 in THF (15 ml) was added water (0.23 g) in THF (15 ml) at −78° C. Gel formation took place during warming to 25° C. over 2 hours. After removal of volatiles in vacuo, a white powder (0.49 g) was obtained which showed negligible organic groups and gave elemental analysis corresponding to stoichiometric $SiO_2.TiO_2$.

Films of stoichiometric $SiO_2.TiO_2$ preferably are prepared by chemical vapor deposition methods. Most preferably, optical films of $SiO_2.TiO_2$ are deposited by atmospheric pressure chemical vapor deposition ("APCVD").

EXAMPLE 3

Optical Films Deposited by APCVD: In solid form, 3.0 grams (amount not critical) of the single source volatile precursor $(^tBuO)_3Si-O-Ti(OBu^t)_3$, obtained as described above in Example 1, was loaded in a stainless steel bubbler and held at 80° C. during the deposition process. Purified nitrogen was used as a carrier gas, with gas feed lines leading to a quartz reaction chamber maintained at 100° C. to prevent condensation of the precursor. Optical films of $SiO_2.TiO_2$ were deposited on glass, quartz and silicon substrates at temperatures ranging from 450°–600° C. The rate of deposition was found to be about 100 Å per minute at 450° C., 150 Å per minute at 500° C., 250 Å per minute at 550° C., and 300 Å per minute at 600° C. The films deposited at 450° C. were found to have a refractive index of 1.73. The films deposited at 500° C. were found to have a refractive index of 1.80. The films deposited at 550° C. were found to have a refractive index of 1.88 and the films deposited at 600° C. were found to have a refractive index of 1.72. An XPS analysis of the films deposited on a silicon substrate showed Si(1s), Si(2s), Ti(3p), O(1s), and C(1s) peaks. The C(1s) peak is believed to be due to surface contamination removable by ion milling a 50 Å layer. The Si(1s) and Ti(3p) peaks are at expected positions for the corresponding oxides. The Si:Ti ratio was found to depend on the deposition temperature, being 1.5:1 for deposition at 450° C., and 1.2:1 at 500° C. and 550° C. Microprobe analysis of the samples showed Si:Ti ratio to be 1:1, with the 550° C. sample showing (at %): Si 16.8 and Ti 16.4. Rutherford backscattering spectra of the samples showed no carbon and a Si:Ti ratio of 1.4, 1.3, 1.2 and 2.1 for films deposited on the silicon substrate at 450° C., 500° C., 550° C. and 600° C., respectively. It will be appreciated by those skilled in the art that these data show the films to contain stoichiometric amounts of silicon and titanium particularly for the films deposited in the 500° C. to 550° C. range.

In view of the present invention, those skilled in this area of technology will recognize various alternatives and modifications which can be made without departing from the true scope and spirit of the invention. All such alternatives and modifications are intended to be included within the scope of the appended claims.

We claim:

1. A novel composition of matter having the formula $(RO)_3Si—O—Ti(OR)_3$ where each R is a tert-butyl moiety.

* * * * *